(12) United States Patent

Canady et al.

(10) Patent No.: US 12,569,288 B2

(45) Date of Patent: Mar. 10, 2026

(54) SYSTEM AND METHOD FOR OPERATING A TOUCHSCREEN IN AN ELECTROSURGICAL GENERATOR

(71) Applicant: Jerome Canady Research Institute for Advanced Biological and Technological Sciences, Takoma Park, MD (US)

(72) Inventors: Jerome Canady, Lakeland, FL (US); Taisen Zhuang, Rockville, MD (US)

(73) Assignee: Jerome Canady Research Institute for Advanced Biological and Technological Sciences, Takoma Park, MD (US)

(*) Notice: Subject to any disclaimer, the term of this patent is extended or adjusted under 35 U.S.C. 154(b) by 837 days.

(21) Appl. No.: 17/468,971

(22) Filed: Sep. 8, 2021

(65) Prior Publication Data

US 2022/0071686 A1 Mar. 10, 2022

Related U.S. Application Data

(60) Provisional application No. 63/075,485, filed on Sep. 8, 2020.

(51) Int. Cl.
A61B 18/12 (2006.01)
A61B 17/00 (2006.01)
(Continued)

(52) U.S. Cl.
CPC ........ A61B 18/1206 (2013.01); A61B 18/042 (2013.01); A61B 2018/00702 (2013.01); A61B 2560/0493 (2013.01)

(58) Field of Classification Search
CPC .............. A61B 18/1206; A61B 18/042; A61B 2018/00702; A61B 2560/0493; A61B 2017/00199; A61B 2034/254; A61B 34/25
See application file for complete search history.

(56) References Cited

U.S. PATENT DOCUMENTS 4,040,426 A 8/1977 Morrison
4,429,694 A 2/1984 McGreevy
(Continued)

FOREIGN PATENT DOCUMENTS

WO 2018191265 A1 10/2018

*Primary Examiner* — Joseph A Stoklosa
*Assistant Examiner* — Annie L Shoulders
(74) *Attorney, Agent, or Firm* — 24IP Law Group USA, PLLC; Timothy R DeWitt

(57) ABSTRACT

A system and method for operating a touchscreen of a gas-enhanced electrosurgical generator. The generator has a display module and a primary controller. The display module has a plurality of touch sensors, a PCB power relay and a CPU. The method comprises selecting electrosurgery settings through a graphical user interface, activating through an input device plasma delivery from the gas-enhanced electrosurgical generator, disabling the plurality of touch sensors through software running on the primary controller, disconnecting power from the plurality of touch sensors with the PCB power relay in response to the disabling of the plurality of touch sensors, applying power to an electrode in the plasma accessory connected to the gas-enhanced electrosurgical generator, and de-activating through an input device plasma delivery from the gas-enhanced electrosurgical generator to the plasma accessory connected to the gas-enhanced electrosurgical generator.

5 Claims, 5 Drawing Sheets

(51) Int. Cl.

| | | |
|---|---|---|
| *A61B 18/00* | (2006.01) | |
| *A61B 18/04* | (2006.01) | |
| *A61B 34/00* | (2016.01) | |

(56) References Cited

U.S. PATENT DOCUMENTS

| | | | |
|---|---|---|---|
| 4,781,175 A | | 11/1988 | Bertrand et al. |
| 5,207,675 A | | 5/1993 | Canady |
| 2013/0296846 A1 | | 11/2013 | Canady et al. |
| 2014/0378892 A1 | | 12/2014 | Keidar et al. |
| 2019/0099179 A1 | * | 4/2019 | Leimbach ........ A61B 17/07207 |
| 2019/0133670 A1 | * | 5/2019 | Hubelbank ........ A61B 18/1206 |
| 2020/0314569 A1 | * | 10/2020 | Morgan ................... H04R 1/22 |
| 2023/0355298 A1 | * | 11/2023 | Shilev ................. A61B 18/042 |

\* cited by examiner

<u>500</u>

530

550

512

510

600

SYSTEM AND METHOD FOR OPERATING A TOUCHSCREEN IN AN ELECTROSURGICAL GENERATOR

CROSS-REFERENCE TO RELATED APPLICATIONS

The present application claims the benefit of the filing date of U.S. Provisional Patent Application Ser. No. 63/075, 485 filed by the present inventors on Sep. 8, 2020.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to gas-enhanced electrosurgical systems, and more particularly, to a touch-screen system for an electrosurgical generator.

Brief Description of the Related Art

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect, and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781, 175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in U.S. Patent Application Publication No. 2013/0296846, which disclosed a system for simultaneously cutting and coagulating tissue. Another system, referred to as a "cold atmospheric plasma" system, is disclosed in U.S. Patent Application Publication No. 2014/0378892.

A gas-enhanced electrosurgical generator is disclosed in WO 2018/191265 entitled "Electrosurgical Gas control Module." The gas-enhanced generator has a housing made of a sturdy material such as plastic or metal similar to materials used for housings of conventional electrosurgical generators. The housing has a removable cover. The housing and cover have means, such as screws, tongue and groove, or other structure for removably securing the cover to the housing. The cover may comprise just the top of the housing or multiple sides, such as the top, right side, and left side, of the housing. The housing may have a plurality of feet or legs attached to the bottom of the housing. The bottom of the housing may have a plurality of vents 118 for venting from the interior of the gas-enhanced generator. On the face of the housing there is a touchscreen display and a plurality of connectors for connecting various accessories to the generator, such as an argon plasma probe, a hybrid plasma probe, a cold atmospheric plasma probe, or any other electrosurgical attachment. There is a gas connector for connecting, for example, a $CO_2$ supply for insufflating an abdomen. The face of the housing is at an angle other than 90 degrees with respect to the top and bottom of the housing to provide for easier viewing and use of the touch screen display by a user. A power module and one or more of the gas control modules may be mounted within the gas-enhanced electrosurgical generator. A gas pressure control system for controlling a plurality of gas control modules is within the gas-enhanced electrosurgical generator

SUMMARY OF THE INVENTION

In a preferred embodiment, the present invention is a system and method for operating a touchscreen of a gas-enhanced electrosurgical generator. The generator has a display module and a primary controller. The display module has a plurality of touch sensors, a PCB power relay and a CPU. The method comprises selecting electrosurgery settings through a graphical user interface displayed on the touchscreen, activating through an input device plasma delivery from the gas-enhanced electrosurgical generator to a plasma accessor connected to the gas-enhanced electrosurgical generator, disabling the plurality of touch sensors through software running on the primary controller in response to the activating plasma delivery, disconnecting power from the plurality of touch sensors with the PCB power relay in response to the disabling of the plurality of touch sensors, applying power to an electrode in the plasma accessory connected to the gas-enhanced electrosurgical generator, de-activating through an input device plasma delivery from the gas-enhanced electrosurgical generator to the plasma accessory connected to the gas-enhanced electrosurgical generator, restoring power to the plurality of touch sensors with the PCB power relay in response to de-activating plasma delivery, enabling the plurality of touch sensors through software running on the primary controller in response to the restoring power to the plurality of touch sensors. The step of activating through an input device plasma delivery from the gas-enhanced electrosurgical generator may comprise activating the plasma though an input device on the plasma accessory connected to the gas-enhanced electrosurgical generator and the comprises an electrosurgical hand piece and the input device comprises a control button on the electrosurgical hand piece. Alternatively, the input device may comprise a foot pedal connected to the gas-enhanced electrosurgical generator. Still further, the input device may comprise a voice activation system built into the generator. The CPU in the display module may comprise and ARM processor.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

The preferred embodiments of the invention are described with reference to the drawings. An electrosurgical or gas-enhanced electrosurgical generator 100 has a front panel 110 and a housing having an interior compartment in which a plurality of modules or other gas or electrical elements are housed. Such other elements may include gas modules, a high frequency power module, a low frequency power module, an RFID reader, processors, or memory. A cover 130 encloses the interior compartment of the housing. The body of the housing also may have a base with support structures for mounting gas and/or power modules in the interior of the base and a plurality of vents, side support members a rear panel, a shield panel, and side rails. The front panel 110 has an opening for receiving a display screen 140, for example a touchscreen display of a tablet computer.

Figure 1:
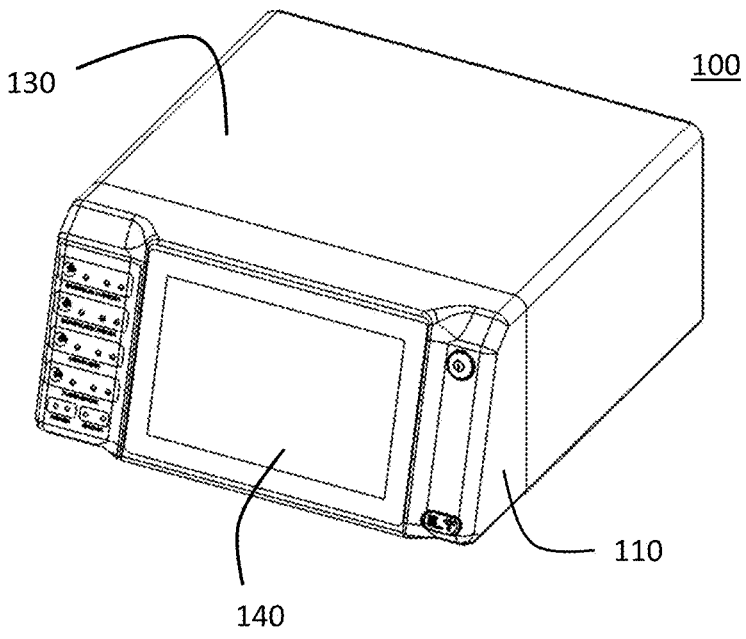
FIG. 1 is an assembly view of an electrosurgical generator housing in accordance with a preferred embodiment of the present invention.
Figure 2:
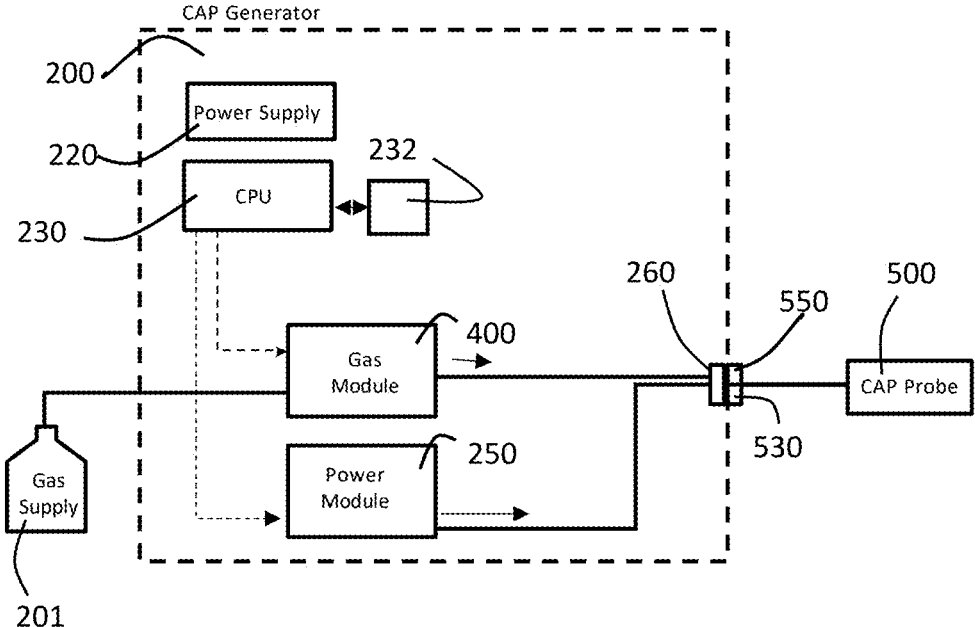
FIG. 2 is a block diagram of a cold atmospheric plasma generator in accordance with a preferred embodiment of the present invention.

As shown in FIG. 2, an exemplary gas-assisted electrosurgical generator 200 has a power supply 220, a CPU (or processor or FPGA) 230 and a memory or storage 232. The system further has a display 140 (FIG. 1), which may be the display of a tablet computer. The CPU or controller 230 controls the system and receives input from a user through a graphical user interface displayed on display 140. The CAP generator further has a gas control module 400 connected to a source 201 of a CAP carrier gas such as helium, argon or other gas. The CAP generator 200 further has a power module 250 for generating low frequency radio frequency (RF) energy, such as is described in U.S. Pat. No. 9,999,462, which is hereby incorporated by reference in its entirety. The power module 250 contains conventional electronics and/or transformers such as are known to provide RF power in electrosurgical generators. For a cold plasma generator, the power module 250 may operate, for example, with a frequency between 10-200 kHz, which is referred to herein as a "low frequency," and output peak voltage from 3 kV to 6 kV and preferably at a frequency near (within 20%) of 40 Hz, 100 Hz or 200 Hz. The gas module 400 and power module 250 are connected to connector 260 that allows for attachment of an applicator 500 to be connected to the generator 100 via a connector having an electrical connector 530 and gas connector 550.

Figure 5:
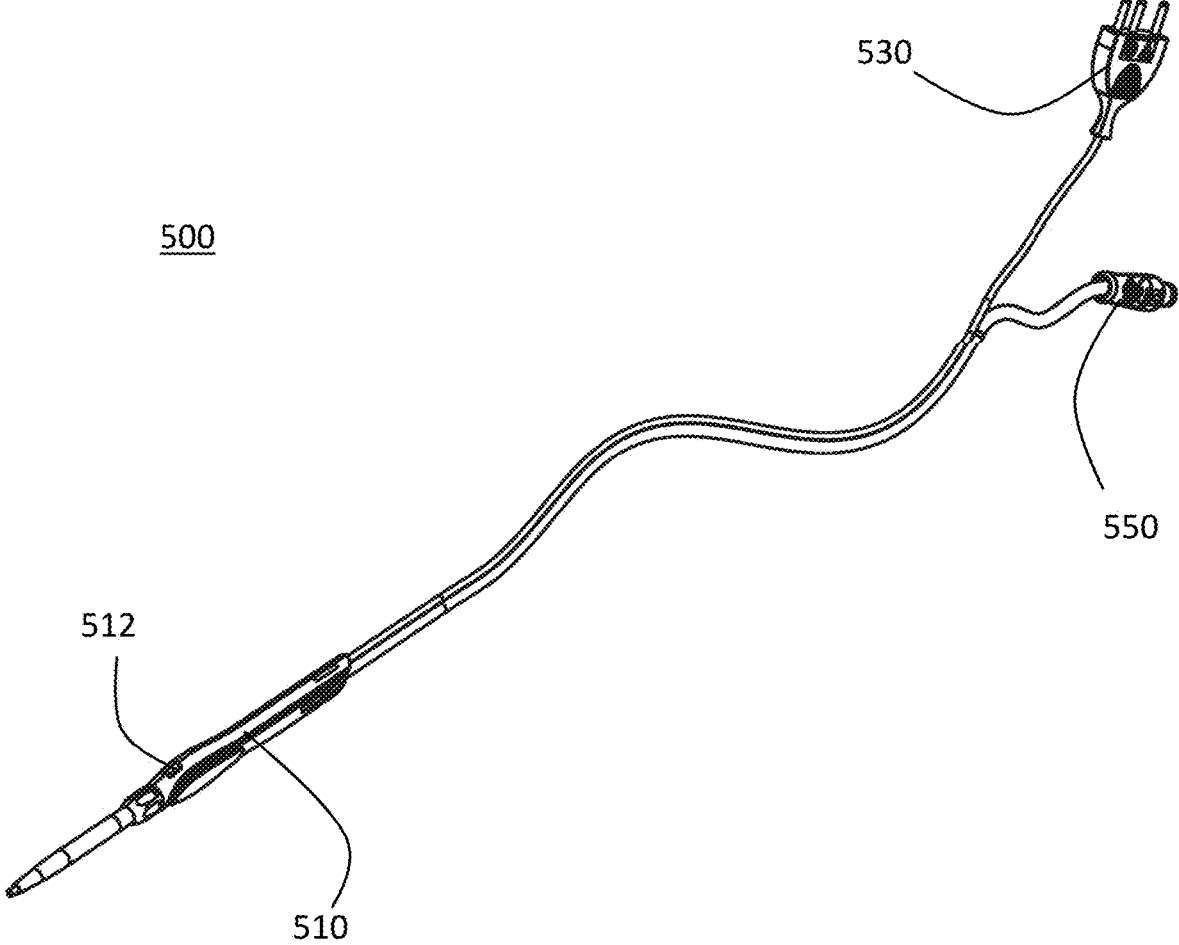
FIG. 5 is a perspective view of an exemplary electrosurgical accessor that may be used with a preferred embodiment of the present invention.
Figure 6:
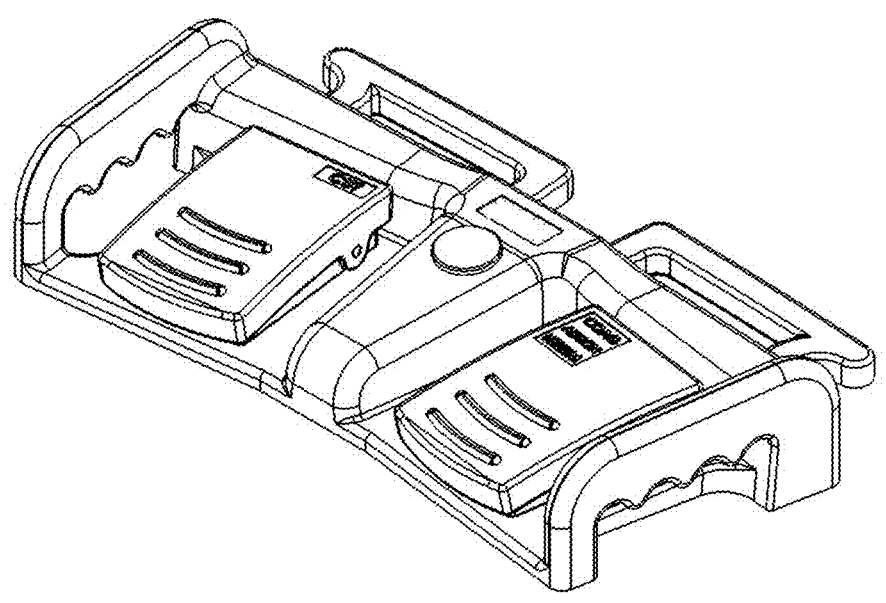
FIG. 6 is a perspective view of an exemplary foot pedal that may be used with a preferred embodiment of the present invention.

Activation of the plasma through an input device may be, for example, through buttons or other controls 512 on a plasma handpiece 510 (see FIG. 5), through a foot pedal 600 (see FIG. 6), or through voice activation. The plasma delivery may be through a handpiece or through a flexible tube such as is used in endoscopy.

Gas-enhanced electrosurgical generators tend to have high EMI (electromagnetic interference) noise during plasma delivery. That EMI noise will interrupt the operation of a projected capacitive (PCAP) touch screen 310. As a result, the touch sensors may be corrupted by EMI noise, which can lead to malfunction of the electro-surgical generator.

Figure 3:
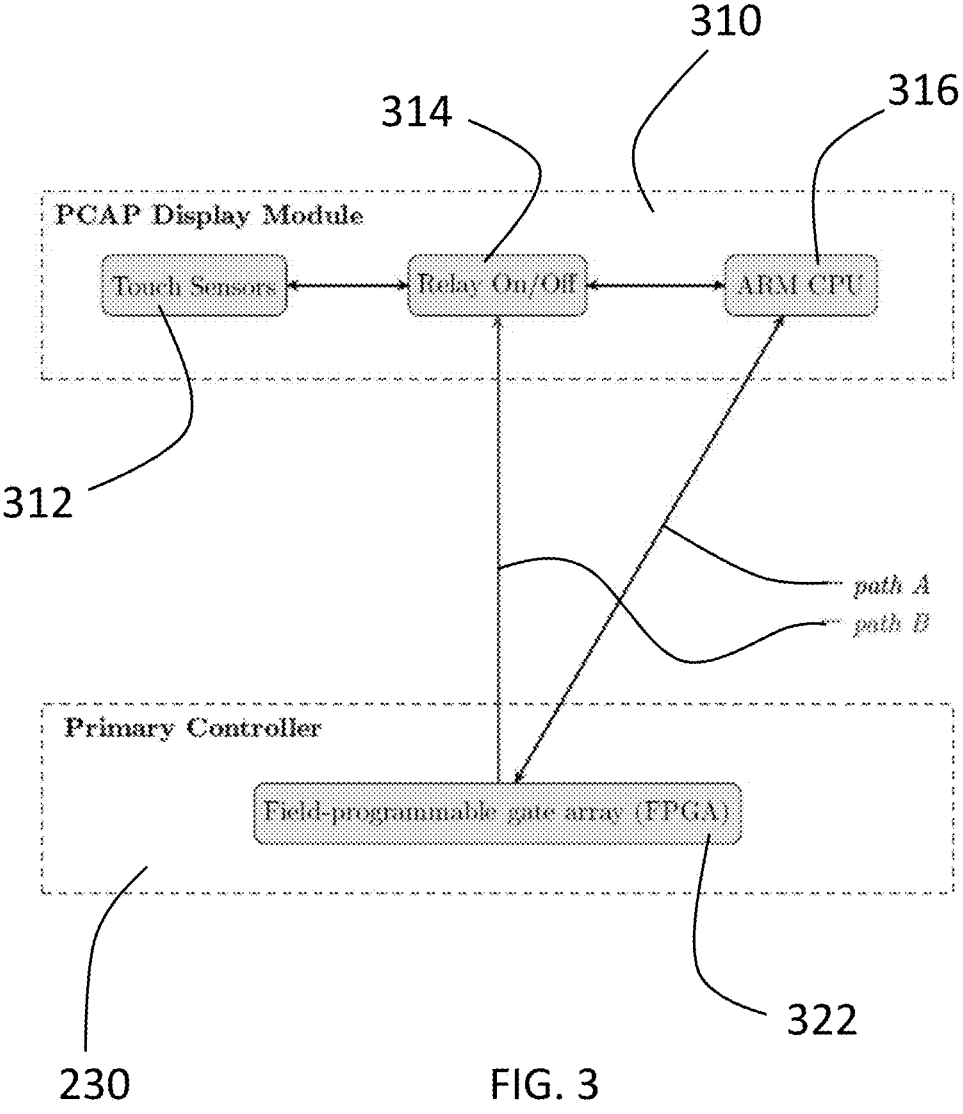
FIG. 3 is a diagram of a system and method for operating a touchscreen in an electrosurgical system in accordance with a preferred embodiment of the present invention.
Figure 4:
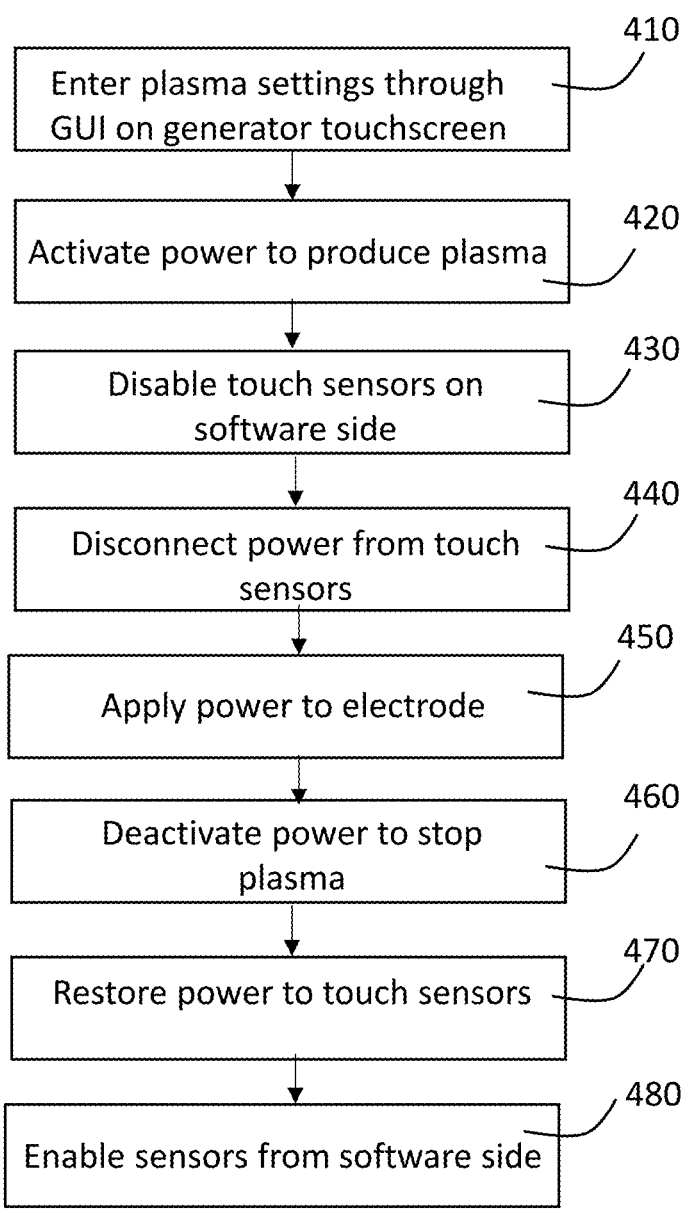
FIG. 4 is a flow chart illustrating a method in accordance with a preferred embodiment of the present invention.

To solve this problem, the present invention incorporates a PCB power relay to resolve the EMI noise issue. As shown in FIGS. 3 and 4, the settings for a particular procedure are entered through a graphical user interface (GUI) running on a primary (FPGA) controller 322 in an electrosurgical generator (410). When the power (plasma) is activated (420) through an input device connected to or in the gas-enhanced electrosurgical generator, the FPGA controller 322 in the generator will request the ARM CPU 316 to disable the touch sensors 312 with a custom tslib plugin, that is, disable the touch sensors from the software side (430), which will disable the entire graphical user interface (GUI). (See path A in FIG. 3.) Then, FPGA 322 will tell PCB relay 314 to disconnect the power supply to the touch sensors (440) so the touch sensors will not be corrupted by EMI noise form the plasma. (See path B in FIG. 3.) Once plasma delivery is stopped (460), the FPGA 322 will ask the PCB relay 314 to restore power the touch sensors (470). Finally, FPGA 322 requests ARM CPU 316 to enable the touch sensors from the software side (480). In this way corruption of the touch sensors by EMI form the plasma is prevented.

The present invention may be used in any electrosurgical generator having touchscreen, regardless of what type of electrosurgery is being performed. This is true for gas-assisted electrosurgery as well as traditional electrosurgery.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for operating a touchscreen in a gas-enhanced electrosurgical generator having a display module and a primary controller, wherein said display module has a plurality of touch sensors, a PCB power relay and a CPU, the method comprising:

selecting electrosurgery settings through a graphical user interface displayed on said touchscreen;

activating through an input device plasma delivery from said gas-enhanced electrosurgical generator to a plasma accessor connected to said gas-enhanced electrosurgical generator;

disabling said plurality of touch sensors through software running on said primary controller in response to said activating plasma delivery;

preventing electromagnetic interference during operation of said plasma delivery by disconnecting power from said plurality of touch sensors with said PCB power relay in response to said disabling of said plurality of touch sensors;

applying power to an electrode in said plasma accessory connected to said gas-enhanced electrosurgical generator;

de-activating through an input device plasma delivery from said gas-enhanced electrosurgical generator to said plasma accessory connected to said gas-enhanced electrosurgical generator;

restoring power to said plurality of touch sensors with said PCB power relay in response to de-activating plasma delivery;

enabling said plurality of touch sensors through software running on said primary controller in response to said restoring power to said plurality of touch sensors.

2. A method for operating a touchscreen in a gas-enhanced electrosurgical generator according to claim 1, wherein said step of activating through an input device plasma delivery from said gas-enhanced electrosurgical generator to a plasma accessory connected to said gas-enhanced electrosurgical generator comprises activating said plasma through an input device in said plasma accessory, wherein said plasma accessory comprises an electrosurgical hand piece and said input device comprises a control button on said electrosurgical hand piece.

3. A method for operating a touchscreen in a gas-enhanced electrosurgical generator according to claim 1, wherein said input device comprises a foot pedal connected to said gas-enhanced electrosurgical generator.

4. A method for operating a touchscreen in a gas-enhanced electrosurgical generator according to claim 1, said input device comprises a voice activation system built into said gas-enhanced electrosurgical generator.

5. A method for operating a touchscreen in a gas-enhanced electrosurgical generator according to claim 1, wherein said CPU comprises an ARM processor.

* * * * *